United States Patent
Rüdinger et al.

(10) Patent No.: US 7,576,228 B2
(45) Date of Patent: Aug. 18, 2009

(54) METHOD FOR THE PRODUCTION OF ISOCYANATOORGANOSILANES

(75) Inventors: Christoph Rüdinger, Starnberg (DE); Ragnar Bogner, Munich (DE); Hans-Jürgen Eberle, Munich (DE); Johann Weis, Sauerlach (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 10/595,174

(22) PCT Filed: Dec. 2, 2004

(86) PCT No.: PCT/ER2004/013724

§ 371 (c)(1), (2), (4) Date: Mar. 17, 2006

(87) PCT Pub. No.: WO2005/056564

PCT Pub. Date: Jun. 23, 2005

(65) Prior Publication Data

US 2007/0066784 A1     Mar. 22, 2007

(30) Foreign Application Priority Data

Dec. 11, 2003   (DE) ............................... 103 58 061

(51) Int. Cl.
*C07F 7/04* (2006.01)
(52) U.S. Cl. ..................... 556/414; 556/400
(58) Field of Classification Search ............. 556/414, 556/400
See application file for complete search history.

(56) References Cited

U.S. PATENT DOCUMENTS

| 3,598,852 A | 8/1971 | Berger |
| 6,008,396 A | 12/1999 | Sheridan et al. |
| 6,084,226 A * | 7/2000 | Greene et al. ............... 219/718 |
| 6,812,361 B2 * | 11/2004 | Kammel et al. .............. 556/414 |

FOREIGN PATENT DOCUMENTS

| EP | 0 649 850 A1 | 4/1995 |
| EP | 0 649 850 B1 | 4/1995 |
| EP | 1 010 704 A2 | 6/2000 |

OTHER PUBLICATIONS

Derwent Abstract Corresponding to EP 010 704 A2.
Mühlbauer et al., "Industrielle Elektrowärmetechnik" [Industrial Electrical Heating Technology], Vulkan-Verlag, Essen, 1992, pp. V-VIII.
Orth et al., "Mikrowellenerwärmung—Anwendungen in der Industrie" [Microwave Heating: Industrial applications], elektrowärme international 49, Aug. 1, pp. B149-B155.
Mingos et al., "The Application of Microwaves to the Processing of Inorganic Materials", British Ceramic Transactions, vol. 91, No. 4, 1992, pp. 124-127.

* cited by examiner

*Primary Examiner*—Daniel K Sullivan
*Assistant Examiner*—Sudhakar Katakam
(74) *Attorney, Agent, or Firm*—Brooks Kushman P.C.

(57) ABSTRACT

A process for preparing isocyanoatoorganosilanes by thermolysis of carbamatoorganosilanes in the presence of microwave radiation, optionally employing homogeneous or heterogeneous catalysis, provides isocyanatoorganosilane product in higher yield than prior art thermolyses, and with fewer byproducts. A continuous process is thus possible.

16 Claims, No Drawings

METHOD FOR THE PRODUCTION OF ISOCYANATOORGANOSILANES

CROSS-REFERENCE TO RELATED APPLICATION

This application is the U.S. national phase of PCT Appln. No. PCT/EP2004/013724 filed Dec. 2, 2004, which claims priority to German application 103 58 061.1 filed Dec. 11, 2003.

BACKGROUND OF THE INVENTION

1. Field of the Invention

The invention relates to a process for preparing isocyanatoorganosilane.

2. Description of the Related Art

For some time there has been great interest in an economic method for preparing isocyanoatoorganosilanes in high yields and purities. Said compounds are of great economic importance since they are used, for example, industrially as adhesion promoters between organic polymers and inorganic materials (also termed coupling agents, crosslinkers).

For their preparation, processes are preferred in which the starting materials are almost completely safe or completely safe in order to facilitate handling and procedure. In the case of the processes previously used, however, isocyanoatoorganosilanes are prepared in relatively low amounts, and in low-efficiency and expensive processes.

For instance, in the process described in U.S. Pat. No. 6,008,396, carbamatoorganosilanes are converted in inert hot media to the isocyanates, with elimination of alcohol. However, this process can only be operated semi-continuously, since the concentration of impurities in the medium, even after a short time, increases in such a manner that the desired purity of the product is no longer ensured.

In the process described in U.S. Pat. No. 3,598,852, carbamatoorganosilanes are vaporized in vacuum and the isocyanatosilane formed is distilled off continuously.

In the process described in EP 1010704 A2 carbamatoorganosilanes are thermally cleaved in the liquid phase to give the corresponding isocyanoatoorganosilanes with catalysis by Sn(II) chloride. Particularly the highly complex process for isolating and purifying the desired products which leads to low yields has been found disadvantageous in this process, and thus it appears not to be of interest for application on an industrial scale.

EP 649850 B1 discloses the thermal cleavage (thermolysis) of carbamatoorganosilanes in the gas phase at atmospheric or reduced pressure. However, the yields obtainable by this process, in particular of isocyanatomethylorganosilanes, are unsatisfactory under the conditions described there.

SUMMARY OF THE INVENTION

The object was therefore to provide a further process for preparing isocyanoatoorganosilanes which solves the problems known from the prior art. This and other objects are achieved by thermolysis of carbamatoorganosilanes induced by exposure to microwave radiation.

DETAILED DESCRIPTION OF THE PREFERRED EMBODIMENT

The object was therefore to provide a further process for preparing isocyanoatoorganosilanes which solves the problems known from the prior art.

The object is achieved by the thermolysis being induced by exposure to microwave radiation.

The invention relates to a process for preparing isocyanoatoorganosilanes by thermolysis of carbamatoorganosilanes wherein the thermolysis takes place by exposure to microwave radiation.

The term "microwaves" is taken to mean here electromagnetic oscillations having a frequency of 300 MHz to 300 GHz.

In a preferred embodiment of the inventive process, isocyanoatoorganosilanes of the general formula (1) are prepared

$$R^2R^3R^4Si\text{—}R^1\text{—}N\text{=}C\text{=}O \qquad (1),$$

where

R is a monovalent $C_1$-$C_{10}$-alkyl radical, $R^1$ is a divalent $C_1$-$C_6$-hydrocarbon radical and $R^2$, $R^3$ and $R^4$ are in each case independently of one another, a methyl, ethyl, n-propyl, isopropyl, methoxy, ethoxy, n-propoxy or isopropoxy radical, by thermolysis of carbamatoorganosilanes of the general formula (2)

$$R^2R^3R^4Si\text{—}R^1\text{—}NH\text{—}CO\text{—}OR \qquad (2).$$

In terms of the selectivity and reaction rate that can be achieved, the inventive process offers significant advantages over the prior-art processes.

In the process, in general $C_1$-$C_{10}$-alcohols of the general formula ROH are eliminated from the carbamatoorganosilanes, in particular those of the general formula (2), by thermolysis, in particular methanol, ethanol, propanol, butanol, isobutanol, pentanol, hexanol, isohexanol, cyclohexanol and 2-ethylhexanol. Preferably, methanol and ethanol, particularly preferably methanol, are eliminated.

By means of the inventive process, it is generally possible to prepare isocyanatoorganosilanes containing short-chain spacers between the Si atom and the isocyanate function, which have been available hitherto only with difficulty and in moderate yields, in particular those isocyanatoorganosilanes of the general formula (1) where $R^1$ is methylene.

As spacer $R^1$ between the organosilyl group and the carbamato group, use can generally be made of linear or branched saturated or unsaturated $C_1$-$C_6$-hydrocarbon groups. Preferred spacers $R^1$ are alkylene radicals, in particular linear alkylene radicals; most preferably, use is made of methylene, ethylene and propylene.

$R^2$, $R^3$ and $R^4$ are preferably methyl, methoxy, ethoxy, n-propoxy or isopropoxy radicals.

By means of the inventive process, in particular compounds of the general formula 1 where $R^2$, $R^3$=methoxy, $R^4$=methyl and $R^1$=methylene; or $R^2$=methoxy, $R^3$=ethoxy, $R^4$=methyl and $R^1$=methylene; or $R^2$, $R^3$=ethoxy, $R^4$=methoxy and $R^1$=methylene; or $R^2$, $R^3$=methoxy, $R^4$=ethoxy and $R^1$=methylene, can be prepared in high yields and purities.

The inventive process can optionally be carried out in the presence of a catalyst. Catalysts which come equally into consideration are in principle homogeneous and heterogeneous catalysts.

Suitable homogeneous catalysts are one or more compounds selected from the group consisting of soluble tin, lead, cadmium, antimony, bismuth, titanium, zirconium, niobium, iron, cobalt, manganese, chromium, molybdenum, tungsten, nickel, copper and zinc compounds, and also soluble organic nitrogen bases.

In particular, suitable compounds are 1,4-diazabicyclo-[2.2.2]octane, dibutyltin dilaurate, dibutyltin maleate, dibutyltin diacetate and dimethyltin dichloride.

As heterogeneous catalysts, use can be made in general of metals and/or compounds comprising elements selected from the group Sn(I), Sn(II), Pb(II), Zn(II), Cu(I), Cu(II), Co(I), Co(II), Na, K, Li, Rb, Cs, Sr, Ba, Mg, Ca, Cr, Mo, Ti, V, W, Ce, Fe, Ni, Si, Al, Ge, Ga, In, Sc, Y, La, lanthanides, Pd, Pt, Co, Rh, Cu, Ag, Au, Zn, Cd, N, B, C, and their mixtures and alloys comprising the abovementioned elements.

Preferred heterogeneous catalysts are oxides, hydroxides, oxyhydroxides, mixed oxides, acetates, formates, oxalates, tartrates, citrates, nitrates, carbonates, or mixtures of the abovementioned compounds of one or more elements selected from the group consisting of Sn(I), Sn(II), Pb(II), Zn(II), Cu(I), Cu(II), Co(I), Co(II), Na, K, Li, Rb, Cs, Sr, Ba, Mg, Ca, Cr, Mo, Ti, V, W, Ce, Fe, Ni, Si, Al, Ge, Ga, In, Sc, Y, La, lanthanides, Pd, Pt, Rh, Cu, Ag, Au and Cd.

In particular, suitable heterogeneous catalysts are those comprising one or more compounds selected from the group consisting of $TiO_2$, $ZrO_2$, $HfO_2$, $Al_2O_3$, BaO, CaO, MgO, $CeO_2$, $La_2O_3$, $Y_2O_3$, $Sm_2O_3$, $Yb_2O_3$, $Cr_2O_3$, ZnO, $V_2O_4$, $MnO_2$, NiO, $In_2O_3$, $Ga_2O_3$, $GeO_2$, FeO, $Fe_2O_3$, $Fe_3O_4$, CuO, $Co_3O_4$, $Fe(MoO_4)_3$, MgO/CsOH, MgO/NaOH, aluminosilicates, in particular zeolites in different pore sizes, cordierite of the composition 2 $MgO.2$ $Al_2O_3.5$ $SiO_2$, heteropolyacids, carbon modifications, e.g. graphite, transition metal nitrides, transition metal borides, transition metal silicides and carbides.

These metals, metal compounds or their mixtures can also be applied to porous or non-porous support materials. Particularly suitable supports made of inert refractory materials are oxidic and nonoxidic ceramic, $SiO_2$, carbon, aluminosilicates, magnesium aluminosilicates or resistant metallic materials, in particular glass wool, quartz wool, ceramics, oxidic compositions, such as $SiO_2$, $Al_2O_3$, $Fe_2O_3$ or steatite.

The catalyst supports can be used in the form of irregular granules, spheres, rings, half-rings, saddles, cylinders, trilobes or monoliths.

The inventive process is generally carried out with microwaves in the frequency range from 300 MHz to 300 GHz, particularly in the ISM frequency bands with the central frequencies of 896 MHz, 915 MHz, 922 MHz, 2.45 GHz, 5.8 GHz, 24.1 GHz, 61 GHz, 122 GHz, 245 GHz, more preferably at 915 MHz, 2.45 GHz and 5.8 GHz. The microwaves are generated using generators having known active components such as electron tubes such as, for example, magnetron, klystron, gyrotron or semiconductor amplifiers. Preference is given to air-cooled or water-cooled magnetrons having individual transmission outputs of 100 W to 100 kW, more preferably 300 W to 30 kW. The reaction, initiated by the irradiation of the reactants with microwaves, must be carried out in a reaction chamber which is suitable for irradiation with microwaves. Suitable materials for the reaction chamber are chemically stable materials permeable to microwaves, such as, for example, microwave-transparent glasses, quartz glass, microwave-transparent oxidic ceramics, microwave-transparent nonoxidic ceramics, or chemically stable materials which are impervious to microwaves, such as, for example, metals which, for the irradiation of the microwaves, are equipped with windows made from microwave-transparent material such as, for example, microwave-transparent glasses, quartz glass, microwave-transparent oxidic ceramics, or microwave-transparent nonoxidic ceramics. The microwaves are coupled radiatively into the reaction chamber via known components such as launchers, hollow wave guides, tuners, circulators, insulators, slot antennas, irises or direct generators.

The reaction chamber can be free or provided with internals. The internals affect the flow distribution, temperature distribution and microwave distribution in the reaction chamber. The internals can consist of microwave-transparent material such as microwave-transparent glasses, quartz glass, microwave-transparent oxidic ceramic, microwave-transparent non-oxidic ceramic and then affect only the fluid flow in the reaction space. If the internals consist of microwave-reflecting material (e.g. high-conductivity metals, graphite) or microwave-absorbent materials (especially ceramics, silicon carbide, magnetic materials or electric resistance materials), the microwave distribution and temperature distribution are also affected.

In the reaction chamber, when the inventive process is optionally carried out in the presence of a catalyst, one or more of the abovementioned heterogeneous catalysts can be present or introduced continuously, together with the internals or alone.

The reaction chamber can also be constructed in such a manner that the entire reaction space or a part of the reaction space is filled with a fluidized solid, the solid being able to act as microwave absorber, heat carrier and/or catalyst.

For the general design of microwave irradiation systems, reference may also be made at this point to literature such as A. Mühlbauer, "Industrielle Elektrowärmetechnik" [Industrial Electrical Heating Technology], Essen Vulkan-Verlag, 1992; D. M. P. Mingos, "The Application of Microwaves to the Processing of Inorganic Materials", British Ceramic Transactions, 91, 1992; G. Orth, "Mikrowellenerwärmung in der Industrie" [Microwave Heating in Industry] RWE-Industrieforum, Essen, 1993.

The process can generally be carried out batchwise, semi-continuously, or continuously. Preference is given to continuously distilling off one or more volatile reaction products from the reaction chamber, both the reaction product alcohol and the reaction product isocyanoatoorganosilane being able to be distilled off separately or together.

In one preferred embodiment of the inventive process the reaction chamber is introduced into a distillation column, forming a reactive distillation. The high-boiling reaction products can be taken off in the liquid phase of the column, below the reaction chamber, while the volatiles can be taken off at the top of the column, above the reaction chamber. Middle fractions may be drawn off not only between the reaction section and the top of the column but also between the reaction section and the liquid phase of the column.

The carbamatoorganosilanes, especially those of the general formula (2), are reacted preferably in a temperature range of 150-500° C., particularly preferably in a range of 200-400° C., in particular in a range of 250-350° C., under microwave irradiation. The temperature here may be attained by microwave irradiation alone or by a combination of conventional heating and microwave radiation. The conventional heating power may be introduced at the same time as or sequentially to the microwave irradiation. A further possibility is to combine the microwave heating with conventional cooling so as to allow a higher microwave radiation intensity to be applied while observing a specified temperature.

The microwave power is selected such that, under the other boundary conditions of the heat balance in the reaction zone, such as heat supply and heat removal via insulation losses, conventional cooling or heating, heat supply and heat removal via the latent heat of the reaction mixture, evaporative cooling of the reaction mixture, cooling or heating by injection of cold and/or hot inert gases and/or liquids or reactants, it is possible to maintain a preselected reaction temperature.

The process can be carried out with or without a carrier gas, e.g., nitrogen, hydrogen, air, noble gases, such as helium or argon, vapors of carbon-containing substances such as carbon monoxide, carbon dioxide, methane, octane, toluene, decalin or tetralin; the carrier component may also be added in liquid form and then not evaporated until it is in the heated zone, forming a gas stream.

By means of the carrier gas, it is possible to dilute, heat or cool the reaction mixture, fluidize and/or transport solids and set defined flow conditions.

The inventive process is preferably carried out in a pressure range of 0.01-100 bar, more preferably at 0.5-40 bar, in particular in a range of 1-10 bar.

The inventive process, compared with the processes known from the prior art, has the great advantage that the desired products can be obtained in a simple downstream distillation step in high purity (>97%). The formation of six-membered isocyanurates observed at high thermal stresses is virtually completely avoided by the present process.

In one specific embodiment of the inventive process the reaction chamber in which microwave irradiation occurs (microwave reaction chamber) is followed by a reaction zone (afterreaction zone) optionally containing a heterogeneous catalyst.

Since, owing to density, gases absorb microwave radiation only to a very small extent, the process can be provided advantageously with an afterreaction zone in which the mixture partly or fully vaporized in the microwave irradiation zone and containing carbamateorganosilane vapor is reacted further to isocyanate organosilanes. Particularly preferred embodiments of the afterreaction zone are gas-phase reactors filled with a heterogeneous catalyst, the heterogeneous catalysts being selected from the abovementioned embodiments optionally applied to the abovementioned support materials.

The examples which follow serve to illustrate the inventive process and are in no way to be viewed as a restriction.

COMPARATIVE EXAMPLE

Preparation of γ-isocyanatopropyltrimethoxysilane from methylcarbamatopropyltrimethoxysilane

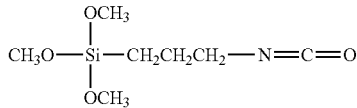

20 ml of methylcarbamatopropyltrimethoxysilane together with 2 g of Fe$_2$O$_3$ catalyst were heated very rapidly to 225° C., using an oil bath, in a glass reaction vessel with distillation still and overhead condenser. Within a reaction time of 60 minutes no overhead condensate was formed. GC analysis of the contents of the still revealed the following composition:
96% by weight methylcarbamatopropyltrimethoxysilane
0.9% by weight γ-isocyanatopropyltrimethoxysilane
0.5% by weight methanol
2.6% by weight by-products

EXAMPLE 1

Preparation of γ-isocyanatopropyltrimethoxysilane from methylcarbamatopropyltrimethoxysilane with microwave irradiation

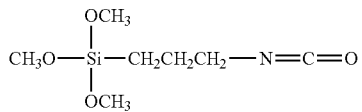

20 ml of methylcarbamatopropyltrimethoxysilane were irradiated with a microwave power of 300 W (frequency 2.45 GHz) in a microwave oven in a glass reaction vessel with distillation still and overhead condenser. Within a reaction time of 5 minutes the overhead temperature rose to 218° C. At this temperature the experiment was ended. 0.7 ml of overhead condensate was formed. GC analysis of the contents of the still revealed the following composition:
90% by weight methylcarbamatopropyltrimethoxysilane
6.1% by weight γ-isocyanatopropyltrimethoxysilane
3.9% by weight by-products GC analysis of the overhead condensate revealed the following composition:
10% by weight methylcarbamatopropyltrimethoxysilane
3% by weight γ-isocyanatopropyltrimethoxysilane
85% by weight methanol Whereas in the comparative example only 0.8 ml of methylcarbamatopropyltrimethoxysilane was converted in 60 minutes, in the inventive example 2.6 ml of methylcarbamatopropyltrimethoxysilane are converted in 5 minutes (40-fold reaction rate).

EXAMPLE 2

Preparation of γ-isocyanatopropyltrimethoxysilane from methylcarbamatopropyltrimethoxysilane with microwave irradiation

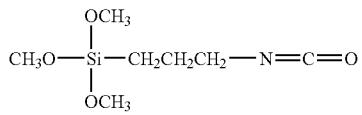

20 ml of methylcarbamatopropyltrimethoxysilane together with 2 g of Fe$_2$O$_3$ catalyst were irradiated with a microwave power of 300 W (frequency 2.45 GHz) in a microwave oven in a glass reaction vessel with distillation still and overhead condenser. Within a reaction time of 4 minutes the overhead temperature rose to 165° C. At this temperature the experiment was ended. 1.7 ml of overhead condensate was formed. GC analysis of the contents of the still revealed the following composition:
85% by weight methylcarbamatopropyltrimethoxysilane
12.5% by weight γ-isocyanatopropyltrimethoxysilane
2.5% by weight by-products GC analysis of the overhead condensate revealed the following composition:
25% by weight methylcarbamatopropyltrimethoxysilane
16% by weight γ-isocyanatopropyltrimethoxysilane
55% by weight methanol Whereas in the comparative example only 0.8 ml of methylcarbamatopropyltrimethoxysilane was converted in 60 minutes, in the inventive example 4 ml of methylcarbamatopropyltrimethoxysilane are converted in 4 minutes (75-fold reaction rate). While in the comparative example by-products are formed in an amount of almost 300% of the target product, the inventive process only gives a by-product fraction of less than 20%.

The invention claimed is:

1. A process for preparing isocyanatoorganosilanes comprising thermolysis of carbamatoorganosilanes in a reactor, wherein the thermolysis takes place in the liquid phase with exposure to microwave radiation, volatile reaction products are removed from the reactor, and an isocyanatoorganosilane product is isolated from the reaction products.

2. The process of claim 1, wherein isocyanatoorganosilanes of the formula (1) are prepared $$R^2R^3R^4Si-R^1-N=C=O \qquad (1),$$

where $R^1$ is a divalent $C_1$-$C_6$-hydrocarbon radical and $R^2$, $R^3$ and $R^4$ are in each case independently of one another, a methyl, ethyl, n-propyl, isopropyl, methoxy, ethoxy, n-propoxy or isopropoxy radical, by thermolysis of carbamatoorganosilanes of the formula (2)

$$R^2R^3R^4Si-R^1-NH-CO-OR \qquad (2),$$

where

R is a monovalent $C_1$-$C_{10}$-alkyl radical.

3. The process of claim 1, wherein the thermolysis takes place in the presence of a catalyst.

4. The process of claim 1, wherein no catalyst is present.

5. The process of claim 3, wherein the catalyst is a homogeneous catalyst.

6. The process of claim 5, wherein the catalyst comprises one or more compounds selected from the group consisting of soluble compounds of tin, lead, cadmium, antimony, bismuth, titanium, zirconium, niobium, iron, cobalt, manganese, chromium, molybdenum, tungsten, nickel, copper, zinc, and soluble organic nitrogen bases.

7. The process of claim 5, wherein the catalyst comprises one or more compounds selected from the group consisting of 1,4-diazabicyclo[2.2.2]octane, dibutyltin dilaurate, dibutyltin maleate, dibutyltin diacetate and dimethyltin dichloride.

8. The process of claim 3, wherein the catalyst is a heterogeneous catalyst.

9. The process of claim 8, wherein the catalyst comprises a metal or compound thereof, the metal selected from the group consisting of Sn(I), Sn(II), Pb(II), Zn(II), Cu(I), Cu(II), Co(I), Co(II), Na, K, Li, Rb, Cs, Sr, Ba, Mg, Ca, Cr, Mo, Ti, V, W, Ce, Fe, Ni, Si, Al, Ge, Ga, In, Sc, Y, La and lanthanides, Pd, Pt, Co, Rh, Cu, Ag, Au, Zn, Cr, Mo, W, Cd, Fe, N, O, B, C, and mixtures and alloys containing the abovementioned elements.

10. The process of claim 8, wherein the catalyst comprises at least one oxide, hydroxide, oxyhydroxide, mixed oxide, acetate, formate, oxalate, tartrate, citrate, nitrate, carbonate, or mixtures of the above-mentioned compounds, of one or more elements selected from the group consisting of Sn(I), Sn(II), Pb(II), Zn(II), Cu(I), Cu(II), Co(I), Co(II), Na, K, Li, Rb, Cs, Sr, Ba, Mg, Ca, Cr, Mo, Ti, V, W, Ce, Fe, Ni, Si, Al, Ge, Ga, In, Sc, Y, La and lanthanides, Pd, Pt, Rh, Ag, Au and Cd.

11. The process as claimed in claim 8, wherein the catalyst comprises one or more compounds selected from the group consisting of $TiO_2$, $ZrO_2$, $HfO_2$, $Al_2O_3$, $BaO$, $CaO$, $MgO$, $CeO_2$, $La_2O_3$, $Y_2O_3$, $Sm_2O_3$, $Yb_2O_3$, $Cr_2O_3$, $ZnO$, $V_2O_4$, $MnO_2$, $NiO$, $In_2O_3$, $Ga_2O_3$, $GeO_2$, $FeO$, $Fe_2O_3$, $Fe_3O_4$, $CuO$, $Co_3O_4$, $Fe(MoO_4)_3$, $MgO/CsOH$, $MgO/NaOH$, aluminosilicates, zeolites, cordierite of the composition $2MgO.2Al_2O_3.5SiO_2$, heteropolyacids, carbon, transition metal nitrides, transition metal borides, transition metal silicides and carbides.

12. The process of claim 8, wherein the catalysts are provided on a support.

13. The process of claim 12, wherein as a catalyst support, an inert refractory material is employed.

14. The process of claim 11, wherein as a catalyst support, oxidic and nonoxidic ceramics, $SiO_2$, carbon, aluminosilicates, magnesium aluminosilicates or resistant metallic materials are used.

15. The process of claim 11, wherein catalyst supports are in the form of irregular granules, spheres, rings, half-rings, saddles, cylinders, trilobes, or monoliths.

16. The process of claim 1, wherein a gas-phase reactor containing a heterogeneous catalyst is located downstream of the microwave reaction chamber.

* * * * *

UNITED STATES PATENT AND TRADEMARK OFFICE
CERTIFICATE OF CORRECTION

PATENT NO. : 7,576,228 B2  
APPLICATION NO. : 10/595174  
DATED : August 18, 2009  
INVENTOR(S) : Christoph Ruedinger et al.

Page 1 of 1

It is certified that error appears in the above-identified patent and that said Letters Patent is hereby corrected as shown below:

Column 7, Line 27, Claim 4:

Delete "claim 1" and insert -- claim 2 --.

Signed and Sealed this

Tenth Day of November, 2009

David J. Kappos  
*Director of the United States Patent and Trademark Office*